(12) United States Patent
Mayer et al.

(10) Patent No.: US 9,339,355 B2
(45) Date of Patent: May 17, 2016

(54) DIVERSION OF MECHANICAL OSCILLATIONS

(71) Applicant: WOODWELDING AG, Stansstad (CH)

(72) Inventors: Jörg Mayer, Niederlenz (CH); Marcel Aeschlimann, Ligerz (CH); Laurent Torriani, Lamboing (CH); Christoph Rusch, Biel (CH); Stéphane Gillieron, Tavannes (CH)

(73) Assignee: WOODWELDING AG, Stansstad (CH)

( * ) Notice: Subject to any disclaimer, the term of this patent is extended or adjusted under 35 U.S.C. 154(b) by 45 days.

(21) Appl. No.: 14/509,527

(22) Filed: Oct. 8, 2014

(65) Prior Publication Data

US 2015/0024343 A1    Jan. 22, 2015

Related U.S. Application Data

(62) Division of application No. 12/281,900, filed as application No. PCT/CH2007/000129 on Mar. 8, 2007, now Pat. No. 8,876,529.

(30) Foreign Application Priority Data

Mar. 9, 2006  (CH) ....................... 376/06

(51) Int. Cl.
| | |
|---|---|
| *A61C 1/07* | (2006.01) |
| *A61C 8/00* | (2006.01) |
| *A61C 3/03* | (2006.01) |
| *A61C 17/20* | (2006.01) |

(Continued)

(52) U.S. Cl.
CPC ............... *A61C 8/0089* (2013.01); *A61B 17/88* (2013.01); *A61C 3/03* (2013.01); *A61C 17/20* (2013.01); *B23Q 11/0032* (2013.01)

(58) Field of Classification Search
CPC ........ A61C 8/0089; A61C 3/03; A61C 17/20; A61C 1/07
USPC ................................ 74/126; 433/86, 119, 118
See application file for complete search history.

(56) References Cited

U.S. PATENT DOCUMENTS 3,505,726 A * 4/1970 Mracek Jaroslav .. B23K 20/106
                                                        228/110.1
3,624,908 A * 12/1971 Ricketts et al. .......... A61C 3/06
                                                         433/118

(Continued)

FOREIGN PATENT DOCUMENTS

CH    671530 A5 *  9/1989  ................ B06B 3/00
DE    201 13 692   11/2001

(Continued)

*Primary Examiner* — Zade Coley
(74) *Attorney, Agent, or Firm* — Rankin, Hill & Clark LLP

(57) ABSTRACT

A device for deflecting mechanical oscillations, at an oscillation receiver location may be set into oscillation along a first axis, and transmits such an oscillation into an oscillation along a second axis at an oscillation output location, wherein the first and the second axis form an angle to one another. The device includes an elongate, bent oscillation element, on whose one end a coupling-in point and at whose other end a coupling-out point is arranged, wherein the device is designed such that the oscillation element oscillates transversally at the coupling-in point and at the coupling-out point, when the oscillation receiver location is subjected to an oscillation.

15 Claims, 7 Drawing Sheets

(51) Int. Cl.
*A61B 17/88* (2006.01)
*B23Q 11/00* (2006.01)

(56) References Cited

U.S. PATENT DOCUMENTS

| | | | | |
|---|---|---|---|---|
| 4,505,676 A | * | 3/1985 | Gonser | A61C 1/07 433/119 |
| 4,820,154 A | * | 4/1989 | Romhild | A61C 1/148 279/80 |
| 4,992,048 A | * | 2/1991 | Goof | A61C 5/023 433/102 |
| 5,094,617 A | * | 3/1992 | Carr | A61C 17/20 433/119 |
| 5,100,321 A | * | 3/1992 | Coss | A61C 3/03 433/118 |
| 5,899,693 A | | 5/1999 | Himeno et al. | |
| 6,139,320 A | * | 10/2000 | Hahn | A61B 17/320068 433/119 |
| 2003/0157458 A1 | * | 8/2003 | Buchanan | A61C 1/07 433/166 |
| 2004/0030341 A1 | * | 2/2004 | Aeschlimann | A61B 17/00491 606/232 |
| 2006/0122543 A1 | * | 6/2006 | Mayer | A61B 17/8875 601/10 |
| 2007/0270833 A1 | | 11/2007 | Bonutti et al. | |
| 2008/0021474 A1 | | 1/2008 | Bonutti et al. | |
| 2008/0039845 A1 | | 2/2008 | Bonutti et al. | |
| 2009/0024161 A1 | | 1/2009 | Bonutti et al. | |
| 2010/0211120 A1 | | 8/2010 | Bonutti et al. | |
| 2010/0299338 A1 | * | 11/2010 | Aarni | H04W 8/22 707/759 |
| 2010/0299597 A1 | * | 11/2010 | Shin | G06F 3/0482 715/702 |
| 2010/0299724 A1 | * | 11/2010 | Masiyowski | H04L 63/105 726/4 |
| 2010/0299789 A1 | * | 11/2010 | Harris | C07K 14/37 800/298 |

FOREIGN PATENT DOCUMENTS

| | | | |
|---|---|---|---|
| EP | 0 535 542 | 4/1993 | |
| EP | 0 594 541 | 4/1994 | |
| EP | 1 530 953 | 5/2005 | |
| FR | 2566262 A1 * | 12/1985 | ............... A61C 3/03 |
| JP | 35-2446 | 3/1960 | |
| WO | 02/069817 | 9/2002 | |
| WO | 2004/017857 | 3/2004 | |
| WO | 2004/017927 | 3/2004 | |
| WO | WO 2005009256 A2 * | 2/2005 | ......... A61B 17/8875 |
| WO | 2008/116203 | 9/2008 | |

* cited by examiner

DIVERSION OF MECHANICAL OSCILLATIONS

BACKGROUND OF THE INVENTION

The invention relates to the application of mechanical oscillations, for example ultrasound oscillations, in situations in which limited spatial conditions limit the freedom of movement. It particularly relates to a device for deflecting mechanical oscillations, in particular to a sonotrode or a coupling piece.

Ultrasound processing apparatus are used increasingly in the medical field, amongst others, in dentistry. One example of an application of ultrasound apparatus in medicine, in particular dentistry, is a newly developed method for anchoring implants and preparations in porous tissue. The method for example is described in the documents WO 02/069,817, WO 2004/017,927 and WO 2004/017,857.

Ultrasound processing apparatus for medical use practically often have an elongate form with a handle, so that they may be used similarly to a dentist's drill in the manner of a hand tool. The, for example, piezoelectric oscillation exciter excites a sonotrode into longitudinal oscillations which transmits these to a tool or a work piece. However, on account of the elongate form of the apparatus, the work at difficulty accessible locations is made more difficult.

A sonotrode is known from EP 0 594 541, which is designed as an annular bending oscillator. The sonotrode oscillates about four node points, which renders possible a deflection of the oscillation about an angle of 90°. The sonotrode may also oscillate about more than four nodes, so that a deflection about another integer divider of 360° is possible, for example about 120°. The disadvantage with the sonotrode of EP 0 594 541 is that it takes up, relatively, much space on account of the annular construction. Moreover, only roughly half of the power coupled into the sonotrode is also coupled out into the tool or work piece. Yet another disadvantage is the fact that a deflection is only possible about angles which are an integer divider of 360°. As a further disadvantage, only small oscillation amplitudes are possible on account of the annular design.

An alternative procedure for the deflection of ultrasound is described in the U.S. Pat. No. 6,139,320. A deflection channel contains a fluid, through which the longitudinal oscillations may be diverted according to the shape of the deflection channel. Thereby, a disadvantage is the fact that energy is lost on account of a certain compressibility of the fluid, and the fluid is thereby heated.

It is accordingly an object of the invention, to provide solutions for the deflection of mechanical oscillations, which overcome the disadvantages of the ideas according to the state of the art and which in particular is suitable for the application with restricted spatial conditions.

Solutions which permit a deflection between an oscillation receiver location and an oscillation output location by roughly 100°-130° are particularly preferred, since the work at difficult to access locations is often particularly easy at these angles.

BRIEF SUMMARY OF THE INVENTION

This object is achieved by the invention as is defined in the patent claims.

A device according to the invention for deflecting mechanical oscillations at an oscillation receiver location, may be set into oscillation along a first axis and transmits such an oscillation into an oscillation along a second axis at an oscillation output location, wherein the first and the second axis form an angle to one another. The device at the oscillation receiver location is designed for connecting an oscillation exciter, and at the oscillation output location for connecting a tool, work piece or intermediate piece. The device is characterised essentially by way of the fact that it comprises an elongate oscillation element bent between two ends, on which a coupling-in point and a coupling-out point are arranged, wherein the device is designed such that the oscillation element oscillates transversally at the coupling-in point and at the coupling-out point, when the oscillation receiver location is subjected to an oscillation.

The mechanical oscillations are, for example, ultrasound oscillations.

The device according to the invention, according to the above teaching, thus acts as a sonotrode, wherein the term "sonotrode" does not mean that the device must engage directly on the tool or work piece, but rather an intermediate piece may also be present, which transmits the oscillations from the sonotrode to a tool or work piece or a further intermediate piece.

By way of the fact that the oscillations are transversely tapped by the oscillation element, the oscillation element acts in the manner of a "hammer" which impinges a tool, work piece or intermediate tool which is lateral with regard to the oscillation element axis, with oscillations.

It has been found that it is possible with the procedure according to the invention, to produce oscillations with a good linearity at the coupling-out point, i.e. oscillations whose component is very small transverse to the desired (transversal with respect to the oscillation element) oscillation direction. It is possible to produce oscillations which run along a very longitudinally extended elliptical path, so that to a very good approximation, one may assume oscillations along a straight line.

A firm, releasable coupling may be present between the device and the tool, work piece or intermediate piece, and also between the oscillation exciter and the device. The result of such a coupling is that the tool, work piece or intermediate piece completely participates in the oscillation at the oscillation output location, i.e. that in each case, both half-waves are transmitted. As an alternative, the transmission may also be effected by way of an only loose contact, wherein then only compression forces and no tensile forces may be transmitted.

The elongate bent design of the oscillation element means that a longitudinal axis and thus a longitudinal direction and transversal directions are defined. The oscillation element may have the shape of a bent rod of any cross section, wherein the cross-sectional area of the rod does not need to be constant over its length. The coupling-in point and the coupling-out point may in each case be located in the vicinity of one end of the rod. Additional elements may be fastened on the rod, for example masses, with which the amplitude ratio between oscillations at the coupling-in point and coupling-out point may be influenced.

One recognition, on which the invention is based, is that the transversal oscillations of such an oscillation element with an elongate, bent section, are suitable for deflecting mechanical vibrations about different angles, which may be almost freely selected by way of the choice of the geometry of the oscillation element.

Preferably, the oscillation element runs in a plane and oscillates in this plane. The deflection angle is determined by the bending of the oscillation element in the plane, as well as by the position of the coupling-in point and of the coupling-out point. An inner side and an outer side are defined by way of the bending in the plane. If the coupling-out point lies on the outer side, the deflection angle corresponds to the bending angle, thus to the angle between the oscillation element longitudinal axis at the coupling-in point and at the coupling-out point. If in contrast, the coupling-out point is located on the inner side, the deflection angle is 180° minus the bending angle.

Under certain circumstances—generally less preferred—a tapping of the oscillation at the oscillation element by an object (tool, work piece or intermediate piece) which is attached on the oscillation at the end side, is also possible. An "outside" coupling-out point then means that the tool, work piece or intermediate piece during the machining lies on the outside with respect to the bending of the oscillation element, and an "inside" coupling-out point inversely means that it lies on the inside.

Practically any deflection angle with a large variability of outer dimensions is made possible by way of the selection of the bending angle and the coupling-in and coupling-out points. In contrast to the state of the art, its outer dimensions may be selected for a given deflection angle, frequency and power, as well as a given amplitude ratio within certain constraints, for example by way of the selection of the mass centers of gravity of two oscillation element halves (corresponding to two oscillation element arms), the selection of coupling-in points and coupling-out points (inside/outside) etc. The oscillation element may, for example, be bent "towards" the tool, work piece or intermediate piece or "away therefrom".

The case in which the bending angle is more than 90°, and the coupling-in point as well as the coupling-out point lie on the outer side, is particularly preferably the case. This is particularly favourable for reasons of space, and a bending angle of more than 90° has been found to be particularly favourable also for reasons of oscillation technology.

The preferred deflection angle is between 100° and approx. 130°, particularly preferably between 110° and 120°. The invention also permits deflection angles which are not integer dividers of 360°.

The oscillation element may, for example, have a shape which corresponds essentially to a sector of an arc of a circle, it may be V-shaped, O-shaped, hook-shaped etc. In embodiments with which it is not the whole oscillation element which is uniformly curved, but with which the curvature is particularly great in a curvature region (for example with the V-shape or Ω-shape), the two arms connecting to the curvature region do not have to be equally long, but the oscillation element may have an asymmetrical shape. In any case, the oscillation element does not form a closed ring but quasi an open ring of a uniform or non-uniform curvature. This is advantageous from several aspects. On the one hand, much greater amplitudes than with an annular sonotrode are possible on account of the non-closed design. On the other hand, with an annular sonotrode, there are several sections between the nodes of the oscillation which oscillate. On application however, the oscillation of each such section is not utilised. The power which is required for setting a non-used section into oscillation is thus lost. For this reason, the efficiency of the design according to the invention is generally greater than an annular sonotrode according to the state of the art. Finally, the non-annular design is also advantageous since, as mentioned, practically infinite deflection angles may be realised, and the space requirement is lower.

The cross section of the oscillation element does not need to be homogenous, but in contrast may vary. Such variations of the cross section or of the arm lengths, as with the material selection, cross-sectional profiles, shape of the oscillation element and mass distribution, as well as positions of the coupling-in point and of the coupling-out point and possible design of joints, additional elements etc., may be used to influence the shape, natural frequencies and amplitude ratios of the natural oscillation. For example, an amplitude amplification or amplitude reduction may be effected by way of the selection of the mass distribution between two arms.

The oscillation element may, for example, be designed similarly to the two arms of a tuning fork, wherein the two arms of the oscillation element, in contrast to tuning forks which are used for tuning musical instruments, do not run parallel to one another, but at an angle, which is adapted to the task.

The oscillation element is connected at the coupling-in point, for example elastically, to an oscillation exciter of the apparatus producing oscillations—for example ultrasound apparatus. An elastic connection means that the stiffness of the connection (more precisely its spring constant) is smaller than the stiffness of the oscillation element itself and also smaller than that of other components of the device.

An elastic connection between the oscillation exciter and the oscillation element permits an oscillation corresponding to the natural oscillation, to be formed with the excitation frequency, without the mass center of gravity of the oscillation element—thus so to say the oscillation element as a whole—having to displace significantly during a deflection. This has a positive effect on the efficiency, since less large masses need to be accelerated.

The connection between the oscillation exciter and the oscillation element according to a first preferred embodiment may comprise a joint, for example an elastic joint. This, for example, acts in a hinge-like manner, i.e. it permits tilt movements in one direction but not in a direction perpendicular thereto. The joint may be attached at the face end of the oscillation element or also laterally. It is preferably designed as one piece with the oscillation element and a fastening element, and may have the shape of a necking, by way of which the material thickness is reduced locally, such that the joint permits pivoting in the oscillation element plane, but not perpendicular thereto.

The fastening element which may optionally be comprised by the device, serves for coupling the oscillation element to the oscillation exciter. It may, for example, be designed as a threaded pin and be screwed directly onto the oscillation exciter. Should the fastening element be designed as one piece with a hinge and the oscillation element, the device under certain circumstances may comprise only a single component, which is also advantageous for the handling and with regard to manufacturing technology aspects.

According to a further embodiment, the connection between a fastening element and the oscillation element or, if the device has no fastening element, directly between the oscillation exciter and the oscillation element, may also be stiff and for example be present as a screwed, bonded or possibly locked-in, riveted or differently designed connection.

If the device comprises a fastening element, the oscillation receiver location is mostly located on this. The fastening element may then be pin-like at least in regions, wherein the oscillation receiver location is located at the one end-face of the pin-like region, and the other end-face connects a transition region to the oscillation element, which also comprises the hinge.

Although a fixed (elastic or stiff) connection between the oscillation exciter and the device according to the invention may be advantageous depending on the application, it is not necessary. Indeed, there need not even be any material connection whatsoever between the oscillation exciter and the device according to the invention, but the connection may also be a loose one. The oscillation exciter may, for example, only be applied onto the device, wherein then the oscillation exciter may only act on the device by way of compressive forces ("only by knocks"), and may exert no tensile forces— the oscillation exciter "hammers" on the device. Thus a coupling between the oscillation exciter and the device only exists for roughly a half wave. In this case, the excitation frequency and the natural frequency of the device are advantageously matched to one another, for example by way of the excitation frequency corresponding to a natural frequency or a harmonic of the natural frequency, or of an integer divider of the natural frequency of the device.

The oscillation output location mostly—but not necessarily—coincides with the coupling-out point of the oscillation element. Suitable coupling arrangements are provided at the oscillation output location, by way of which the tool, work piece or intermediate piece may be temporarily connected to the device such that a user of the apparatus during the impinging of the tool, work piece or intermediate piece with mechanical oscillations, may guide this to the necessary extent, and in particular exert a pressure thereon.

One coupling arrangement at the oscillation output location (thus mostly at the coupling-out point) may, for example, contain a coupling pin on the device, and which may engage into a corresponding hole in the tool, work piece or an intermediate piece. Such a pin may have any shape, for example a cylindrical one with any cross-sectional shape, or a conical one. However, inversely, a hole may be present in the device and a corresponding pin present in the tool, work piece or intermediate piece. These coupling arrangements are particularly simple in manufacture and handling. Depending on the situation, there however exists the danger of a jamming and angle errors may be produced.

Alternatively to the pin-hole coupling, a ball socket may be present on the oscillation element or on the tool/work piece/intermediate piece, which cooperates with a corresponding ball of the counter-piece. A jamming is avoided by way of this. A ball socket which is rotationally secured by way of it not being cylinder-symmetrical, may be used in situations where the orientation of the tool/work piece/intermediate piece during the machining must be defined by the apparatus producing oscillation—and in particular in which rotations about a longitudinal axis are to be prevented. An analogous solution is also conceivable for the pin-hole connection, with which one selects a shape which in cross section is polygonal or is not rotationally symmetrical in another manner, in place of a rotation-cylindrical shape.

A fixed, elastic or a stiff connection between the device and the tool, work piece or intermediate piece, is not absolutely necessary, also at the oscillation output location. Rather, there, the connection—in a guided or unguided manner— may lie in the device being applied onto the tool, work piece or intermediate piece and acting in the manner of a hammer. In the case of a fixed connection, a coupling may contain additional arrangements, by way of which tensile forces may be transmitted onto the tool, work piece or intermediate piece. Such separate arrangements, in the manner known per se, may comprise elements engaging behind one another and running transversely to the vibration direction, for example in the manner of a bayonet locking, a thread or in another manner known per se.

The oscillation element may, for example, be manufactured of titanium or stainless steel. Alternatively to this, according to a particular embodiment, one uses a material for the oscillation element which has a permanent strength, i.e. whose stress-number curve tends asymptotically to a value different to zero, for a large number of load changes. Such materials generally have a cubic-space-centred structure. Examples of this are ferritic steel, for example spring steel. This is not the case for titanium or also for aluminium (a different usable material). Despite this, these materials are potentially suitable if the oscillation deflections of the oscillation element are small in operation in comparison to the maximal possible deflection. Other possible materials are ceramics, metallic glasses or possibly other glasses etc.

The subject matter of the invention is also an appliance for deflecting mechanical oscillation containing a first and a second device, which are designed in each case according to teaching specified above, wherein the oscillation output location of the first device is coupled to the oscillation receiver location of the second device, in a manner such that a transversal oscillation of the first device at its coupling-out point produces a transversal oscillation of the second device at its coupling-in point. The range of the accessible deflection angle may be extended once again in comparison to the individual device by way of this appliance. Moreover, an additional variability results. In particular, a deflection in two planes is possible. For example, the second device may be controlled and rotated relative to the first device. A suitable rotation direction may then be operated from the hand grip or via a suitable remote control, so that the user does not have to directly handle the devices, which are not accessible in some situations. Alternatively to this, the device may be also designed such that the two devices are fixed to one another at a defined angle. This defined angle may, for example, be adapted ex situ.

One of the coupling arrangements discussed above may be present on the second device at the oscillation output location, by way of which a tool, work piece (for example implant) or an intermediate piece is coupled to the second device.

An ultrasound apparatus has an oscillation exciter, oscillation exciter activating electronics and a device or an appliance, which is designed according to the above teaching.

The ultrasound apparatus in the case of a fixed coupling between the oscillation exciter and the device (sonotrode) is preferably operated such that the excitation frequency lies below the (first) natural frequency of the oscillation element. An excitation frequency which is different from the natural frequency is advantageous because then, the output amplitude may be easily controlled by way of the selection of the input amplitude. In contrast to this, with an operation in resonance, the amplitude of the oscillation element (or of the oscillation at the coupling-out point) is very difficult to control. Moreover, the oscillation element and the oscillation exciter do not need to be matched to one another in calibration. If the excitation frequency were to lie above the natural frequency, then a frequency reduction on account of a large load during the application, may lead to the frequency approaching the resonant frequency. With a loose coupling between the oscillation exciter and the device, the excitation frequency may correspond to the resonant frequency or to an integer divider of this.

The operating frequency of the ultrasound apparatus preferably lies between 15 kHz and 40 kHz. With an operating frequency of 20 kHz, the resonant frequency of the oscillation element should preferably be at least 1 kHz, even better at least 2 kHz higher than this. Very generally, the apparatus is operated advantageously at least 5% below the resonant frequency of the oscillation element.

The power of the ultrasound apparatus (i.e. the useful power of the oscillation exciter) is for example between 20 W and 150 W for the implantation of dental implants, and the amplitude (after deflection) of the oscillation lies in the region between 10 μm and 80 μm, for example between 20 μm and 80 μm. The required power depends on the mass of the tool/work piece (as the case may be, including possible intermediate pieces), on the damping, on coefficients of friction, etc. Under certain circumstances, it is only about ⅕ of the above value for the CMF implants which are relatively small compared to dental implants. The power of the ultrasound apparatus and the amplitude, depending on the nature of the implant (a fastening arrangement for a larger implant, for example a pin for fastening a ball socket is valid as such) may vary in a large range for the implantation of implants for other surgical applications. The powers depend greatly on the selected application. They may lie, for example, between 0.5 W and 300 W or more—for example up to 2 kW—the amplitudes may lie between 5 μm and 200 mm.

The desired power determines the moment of inertia of the device. The stiffness of the oscillation element is an important factor for this, which for its part is also determined by the cross-sectional area. With an oscillation element of titanium for the implantation of dental implants at frequencies of 20 kHz, the cross-sectional area may, for example, be between 10 and 50 mm$^2$.

A method for impinging an object with longitudinal, mechanical oscillations and a surgical method are likewise the subject matter of the invention.

The device according to the invention and the appliance which is based on it and the ultrasound apparatus are particularly advantageous in combination with surgical methods, since situations always occur, in which the space which is available is very limited and the ultrasound apparatus may not be applied in any orientation.

The method according to the invention and the ultrasound apparatus according to the invention are on the one hand particularly advantageous with the application in dentistry, cranio-maxillo-facial surgery and minimal invasive surgery (MIS). According to the initially mentioned, newly developed methods for fastening implants and preparations in porous material, the implant or the preparation are impinged with mechanical oscillation in situ, i.e. on the patient, and are driven into the anchoring material. The device according to the invention permits the deflection of the mechanical oscillation about any angle, in particular about angles in the region of about 110° to 120° which are ergonomically favourable with intra-oral access, and which for example dental drilling apparatus also envisage as an angle between the grip and the drill. The device only requires little space in the mouth, and the operating height is low, on account of the shape according to the invention. This permits work also under difficult conditions, with patients who find it difficult to open the mouth wide, and far to the rear in the mouth. The device according to the invention is also advantageous for other applications in the cranio-maxillo-facial (CMF) field of surgery. The invention also has advantages in the field of engineering, in particular precision engineering.

The device particularly preferably comprises a cover in the manner of a protective housing, which amongst other things may serve for preventing secondary damage, by way of it shielding the body and tissue parts from the mechanically oscillating device. The cover may simultaneously also comprise a guide arrangement for holding and guiding the tool, work piece or intermediate piece One may envisage the outer dimensions of such a protective housing being kept as low as possible for purposes of minimal invasive surgery. For example, the device and the housing which surrounds it may be dimensioned such that it would have space in a cylindrical tube with an inner diameter of maximally 8 mm.

Likewise, the device according to the invention, the appliance according to the invention and the ultrasound apparatus according to the invention on the other hand are particularly advantageous for applications in implantation surgery and bone surgery. For example, the sonotrode designed as a device according to the invention may also be advantageous with surgical operations in combination with joint implants and spinal column implants. It is generally suitable for fastening implants at difficulty accessible locations in the human body, for example for fastening intervertebral disk implants between vertebrae. It is likewise suitable for example for fixing the body's own tissue parts relative to one another.

A use of the device according to the invention, the appliance according to the invention or the ultrasound apparatus according to the invention, may also be advantageous for applications as are described in the international published application document WO 2005/009 256.

BRIEF DESCRIPTION OF THE DRAWINGS

Embodiment forms of the invention are explained in detail hereinafter by way of drawings. In the drawings there are shown in.

DETAILED DESCRIPTION OF THE INVENTION

Figure 1:
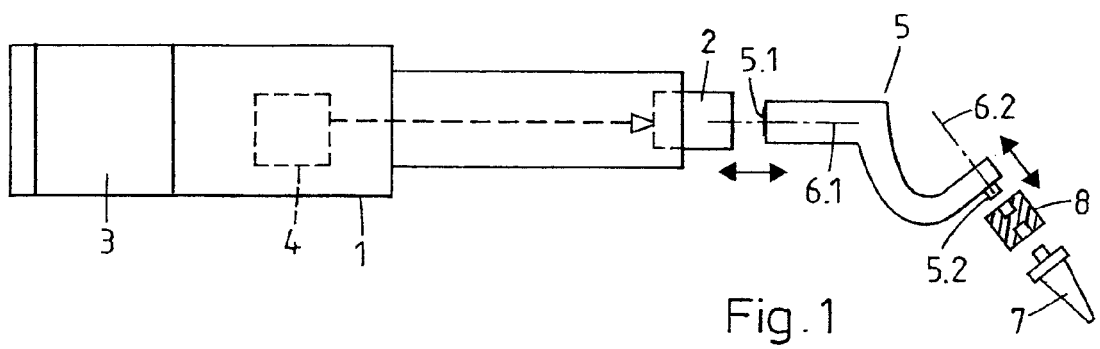
FIG. 1 a schematic representation of an ultrasound apparatus with a sonotrode which is drawn set back, as well as of an implant and an intermediate piece, FIG. 2 a view of a first embodiment of a sonotrode according to the invention, FIGS. 3a and 3b a view of two variants of a second embodiment of a sonotrode according to the invention, FIG. 4 a view of a third, multi-part embodiment of a sonotrode according to the invention, FIGS. 5a to 5j schematic representations of possible shapes of the oscillation element, FIGS. 6a to 6d schematic representations of possible coupling shapes for coupling the oscillation element to a tool, work piece or intermediate piece, FIGS. 7a to 7e in each case, a schematic representation of a joint shape for coupling the oscillation element to a fastening element, FIG. 8 an arrangement with a first and a second sonotrode, FIG. 9 one example for coupling two sonotrodes such that the second sonotrode may not be rotated relative to the first sonotrode, FIG. 10 an application example, specifically the fixation of a joint socket, FIGS. 11 and 12 in each case, a further application example from joint surgery, specifically the fixation of a tibia-plateau implant (artificial tibia head) in two different manners, FIG. 13 one application example from spinal column surgery, specifically the fixation of an intervertebral disk to a vertebral body, FIG. 14 a further example from spinal column surgery, specifically the fastening of a stabilising plate, FIG. 15 a device according to the invention, with a protective housing, and FIG. 16 a view of a further embodiment of a sonotrode according to the invention.

The schematically represented ultrasound apparatus according to FIG. 1 is suitable for use as a hand apparatus. In the known manner, in a housing 1, it contains a non-shown piezo oscillation quartz and a transmission arrangement for transmitting an oscillation of this to an excitation exciter 2. The housing has an elongate basic shape, which is typical of instruments for dental application. A hand grip 3 is also schematically indicated in the drawing. Activation and excitation electronics 4, which provide an output voltage which sets the piezo-oscillation quartz into oscillation with the desired frequency and amplitude, are likewise shown in a schematic manner.

One may further recognise a sonotrode 5 in FIG. 1, which serves for the deflection of mechanical oscillations, which are tapped at the oscillation exciter 2. If an oscillation receiver location 5.1 of the sonotrode is set into oscillation along the first axis 6.1 by way of the oscillation exciter, this produces an oscillation of an oscillation output location 5.2 along a second axis 6.2 which forms an angle α (deflection angle) to the first axis 6.1.

Likewise shown in a schematic manner in FIG. 1, are a dental implant 7 and a plastic element 8 serving as an intermediate piece or a connection piece (for example of PEEK, a plastic which may be mechanical and thermally loaded to a great extent).

The sonotrode may be rotatable about its first axis 6.1, depending on the application purpose and embodiment, which for example makes sense if the ultrasound apparatus is not essentially cylindrical as is shown, but has a different shape which is not cylindrically symmetrical.

Figure 2:
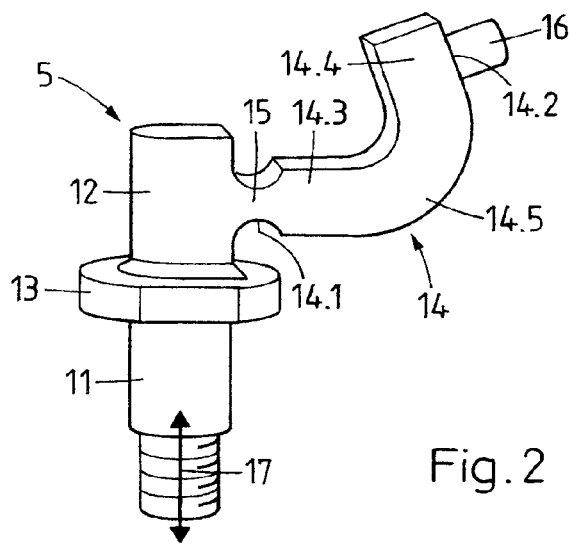

A first embodiment for a specific design of the sonotrode 5 according to the invention is shown in FIG. 2. The fastening element contains a threaded pin 11. This is limited towards a transition region 12 by a collar 13. The oscillation element 14 is coupled at a face end to the transition region 12 by way of a connecting joint 15. The oscillation output location coincides with the coupling-out point 14.2, at which the oscillation element comprises a coupling pin 16, to which—possibly via an intermediate piece—a work piece (an implant for example) or a tool may be coupled.

If the sonotrode at the oscillation receiver location is excited by an oscillation in the direction of the arrow 17—the oscillation corresponds to a longitudinal oscillation of the threaded pin—then a transversal oscillation of the oscillation element is excited at the coupling-in point via the joint 15 which defines the coupling-in point 14.1. A (fundamental) oscillation arises, with which the first arm 14.3 and the second arm 14.4 of the V-shaped oscillation element oscillate to one another in the manner of a tuning fork. On account of the action of the hinge-like joint, this oscillation does not entail a corresponding oscillation of the oscillation element mass center of gravity, but rather the first arm may "tilt away" from the transition region to the top or the bottom, so that a neutral point 14.5 remains roughly stationary with the oscillation. The angle between the longitudinal direction of the oscillation element at the coupling-in point 14.1 and the longitudinal direction at the coupling-out point is 110°, i.e. the angle between the two arms 14.3, 14.4 is roughly 70°.

The cross-sectional shape (in a cross section perpendicular to the longitude direction) of the oscillation element is roughly rectangular, such that the element has a greater width in the direction perpendicular to the plane of the drawing than in the other direction. This helps to suppress oscillations perpendicular to the oscillation element plane.

Figure 3A:
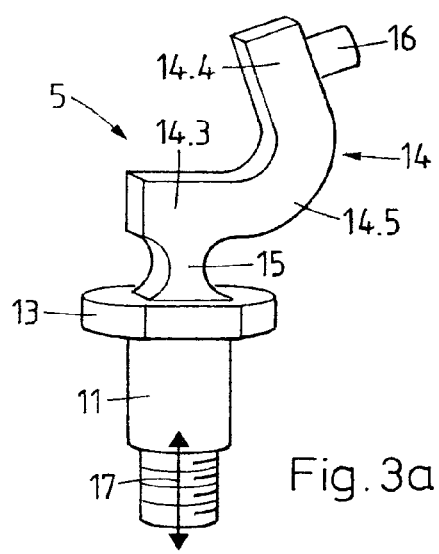

The embodiment of the sonotrode according to FIG. 3a differs from that of FIG. 2 in that the joint 15 does not connect on the end side, but laterally to the oscillation element. A more compact construction manner is made possible by way of this, since the transition region of the sonotrode according to FIG. 2 may be done away with. The joint 15 is quasi knocked on account of a longitudinal oscillation (in the direction of the arrow 17) of fastening element 11. However, it has a similar effect as in FIG. 2, i.e. it permits a tilting-away of the oscillation element, by which means the neutral point 14.5 may remain roughly stationary with the oscillation.

Figure 3B:
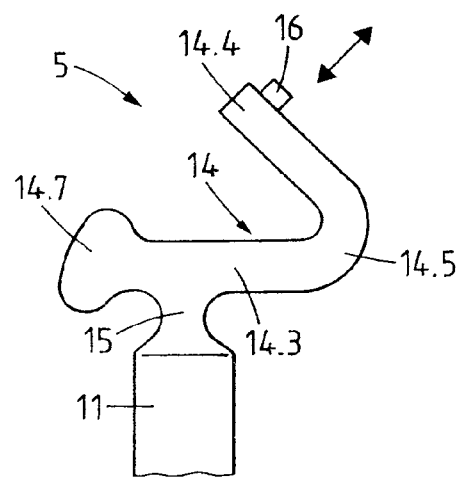

The—only schematically represented—variant of FIG. 3b differs from that of FIG. 3a in that an additional mass 14.7 is present in the region of the first arm 14.3. The resonance characteristics of the device and thus the oscillation behaviour at the oscillation output location and the loads in the region of the hinge 15 and the neutral point 14.5 may be influenced and optimised by way of this. The device according to FIG. 3b accordingly comprises:

a fastening element 11 which oscillates longitudinally on operation, which for example may be designed as a threaded pin, a hinge 15 which connects thereto in the longitudinal direction, an oscillation element 14 which is fastened on the hinge, and with a first arm 14.3 and a second arm 14.4, wherein the hinge 15 is attached on the first arm, and wherein the two arms may be straight or bent, a bent or greatly bent region which is located between the first arm and the second arm, wherein a transition between the hinge 15 and the first arm 14.3 is lateral with respect to the first arm, wherein a counter-mass is present on the first arm on a side of the first arm 14.3 which lies opposite the bent region with respect to the mentioned transition (i.e. the first arm extends "to the rear" beyond the transition).

and wherein the fastening element and the oscillation element are of one piece.

Figure 4:
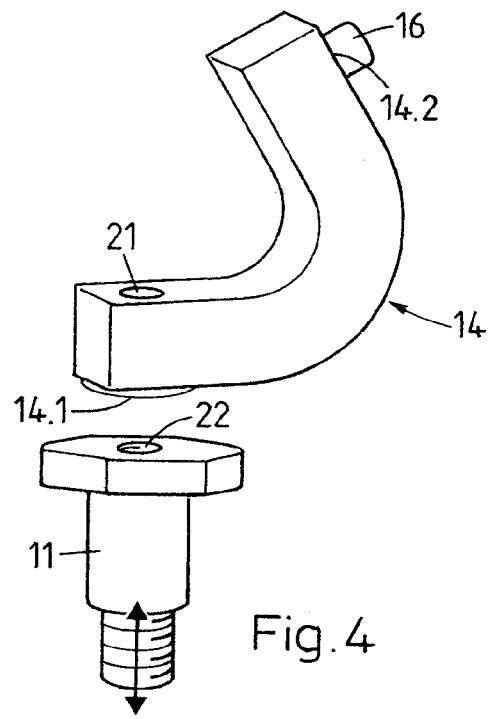

The embodiment according to FIG. 4 is similar to that of FIGS. 3a and 3b, but differs from this in that the sonotrode 5 is not of one piece, but the fastening element 11 is separate from the oscillation element and may be coupled to this by way of a connection element, for example a screw (not drawn). Visible in the Figure are a through-hole 21 for the screw, in the oscillation element, and a corresponding pocket hole 22 in the fastening element 11. In each case the screwed connection may be essentially fixed or it may likewise act as a joint, depending on the elasticity of the screw material, as will yet be explained further below.

Figure 16:
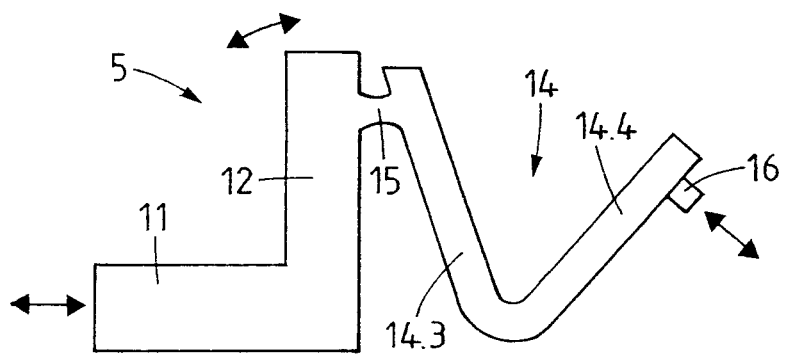

Whereas the oscillation excitation is effected "in axis" in the embodiments of the FIGS. 2-4, i.e. the elements between the oscillation exciter 2 and the oscillation element 14 all lie on a common axis—alternative possibilities are also conceivable. One such alternative possibility is illustrated very schematically in FIG. 16. The fastening element has an L-shape, so that the application point of the oscillation element 14—formed by the hinge 15—is arranged offset from the axis. Apart from the different geometry—this may be advantageous depending on the application—the result of this is that the transition region 12 may be set into tilt oscillations relative to the threaded pin 11. These may have an influence on resonances of the system and on the amplitude at the oscillation output location.

Very many schematic possible shapes of oscillation elements of a sonotrode according to the invention are drawn in the FIGS. 5a to 5i. The oscillation elements may—as the case may be via joints—be fastened to any fastening elements or directly on the oscillation exciter, or be formed as one piece with the fastening elements. They may comprise different coupling arrangements. With all oscillation elements, one assumes a deflection angle of roughly 100°-120°, and respective modifications for other angles are of course not only possible, but also evident.

Figure 5A:
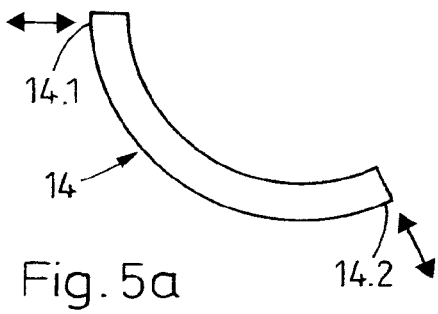

The oscillation element 14 according to FIG. 5a is arc-shaped, i.e. is curved over its whole length, wherein the curvature angle may be constant, but does not need to be constant.

Figure 5B:
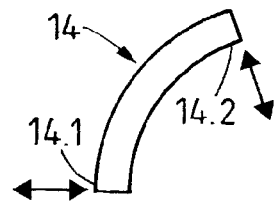

The oscillation element according to FIG. 5b is also arc-shaped. It differs from that according to FIG. 5a in that the coupling-out point 14.2 lies on the inner side, which is why the bending angle is 180° minus the deflection angle. The oscillation element is curved towards the work piece, tool or intermediate piece.

With the variants of the oscillation element which are drawn in the following, the coupling-out point in each case is on the outer side. Modifications in the case of an inner coupling-out point are, however, possible in each of the drawn cases. In the case that the deflection angle is to lie in the region between 100° and 130°, such a modification entails a change of the bending angle to between 50° and 80°. As a whole, a range of bending angles between 50° and 130° which is generally of interest, results.

Figure 5C:
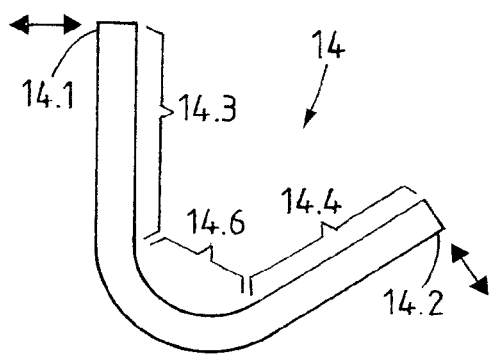

The oscillation element according to FIG. 5c is V-shaped, i.e. two arms 14.3, 14.4 connect to the bent section 14.6. The two arms may, but need not have the same dimensions (length, cross-sectional area or course of the cross-sectional areas) or the same shaping (cross-sectional shape, surface nature etc.)

Figure 5D:
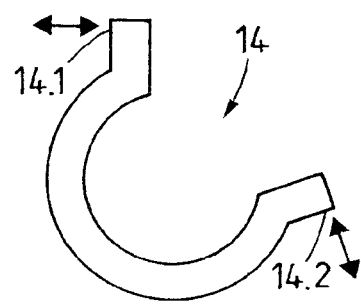
Figure 5E:
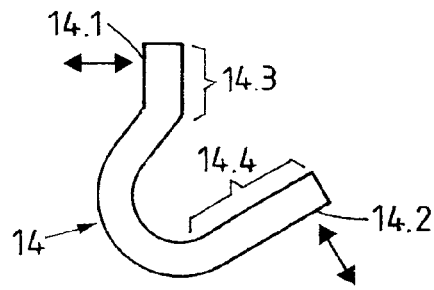

FIG. 5d shows an omega-shaped oscillation element, whilst FIG. 5e shows a hook-like oscillation element. The hook-like oscillation element may be observed as a combination of the concepts of an omega-like oscillation element (first arm 14.3) with a V-shaped oscillation element (second arm 14.4). Very generally, such combinations are possible thus, also arc-shaped-V-shaped, arc-shaped-omega-shaped etc.

Figure 5F:
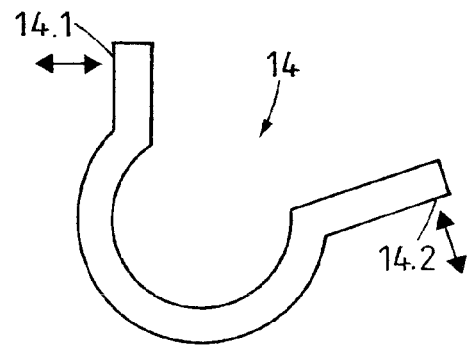

In FIG. 5f, one sees an oscillation element which quasi may be observed as an intermediate solution between an omega-shaped and a V-shaped oscillation element. Such an oscillation element acts similarly to a V-shaped oscillation element, but is stress-optimised.

Figure 5G:
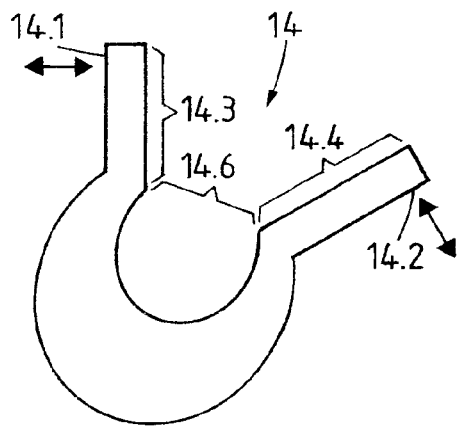
Figure 5H:
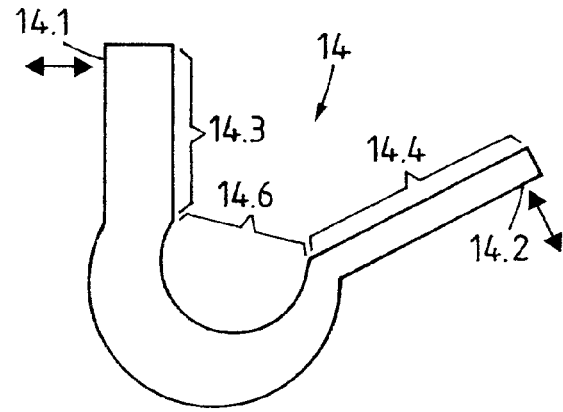

FIG. 5g shows one variant of the oscillation element of FIG. 5f, wherein the thickness (thus the cross-sectional area) in the bent section 14.5 is enlarged compared to the arms 14.3, 14.4. Such an oscillation element is somewhat stiffer than that of FIG. 5f, thus has a higher natural frequency with given material characteristics The oscillation element of FIG. 5h is likewise one variant of that of FIG. 5f, wherein the two arms 14.3, 14.4 have different thicknesses and as a result also different masses. If as drawn, the arm 14.3 with the coupling-in point has the larger mass, the oscillation element effects an amplitude amplification.

Figure 5I:
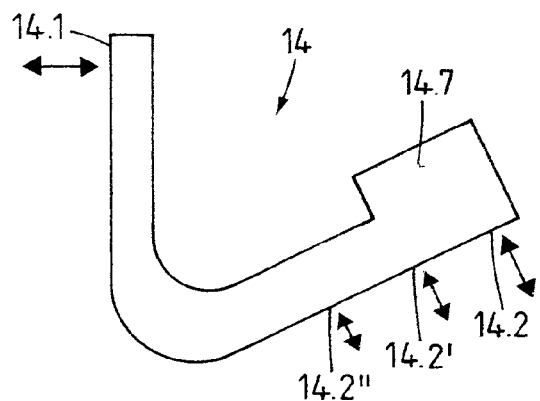

Vice versa, the oscillation element of FIG. 5i, a variant of the oscillation element of FIG. 5c, has an extra mass 14.7 in the region of the coupling-out point, which results in a stepping down of the amplitude.

Figure 5J:
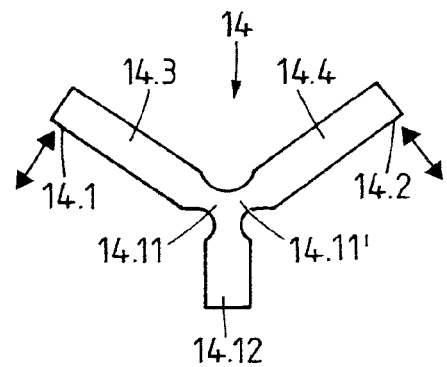

The oscillation element 14 of FIG. 5j between a middle part 14.12 and the two arms 14.3, 14.4 in each case has a hinge-like narrowing 14.11, 14.2. The narrowing reduces the stiffness of the oscillation element as a whole, and thereby, given the same size compared to an oscillation element as in FIG. 5c, steps down the resonant frequency and thus, depending on the operating parameters, also the optimal working frequency. It is also possible to dimension the oscillation element according to FIG. 5j comparatively smaller. By way of this, one may design the oscillation element such that with the same materials, the resonant frequency is in a similar region as with a larger oscillation element according to FIG. 5c. A reduced stiffness of the oscillation element is, thus, a way to miniaturize the oscillation and with this, the whole device.

The variants of the FIGS. 5g-5i may also be applied to the oscillation elements of the FIGS. 5a to 5e or 5a, 5b and 5d to 5f. Combinations of the variants amongst one another are also possible.

FIGS. 6a to 6d show examples of coupling elements. In each case, an arm of an oscillation element 14 which is on the coupling-out side is drawn in two different views or sectioned representations in the figures.

Figure 6A:
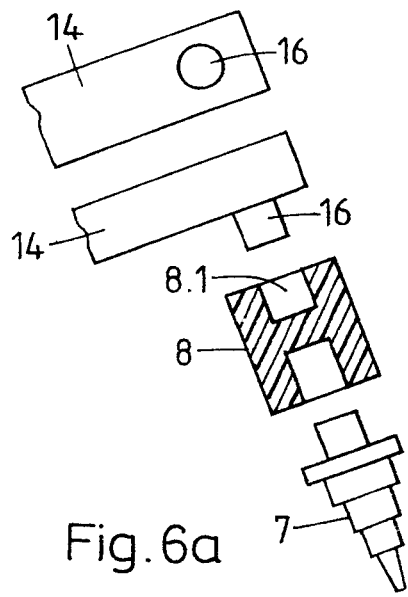
Figure 6B:
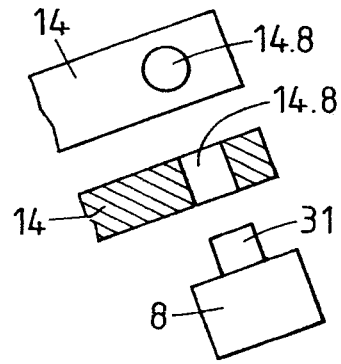

The coupling according to FIG. 6a is effected by the interplay of a coupling pin 16 with a corresponding recess 8.1 in the connection piece 8. The reverse arrangement (hole 14.8 in the oscillation element, pin 31 on the connection piece) is shown in FIG. 6b. This type of coupling is simple in manufacture and permits a simple coupling, but is however prone to angle errors and is not rotationally secure. If instead of a circularly cylindrical pin, one uses a different pin which is not cylinder-symmetrical—a polygonal, elliptical, star-shaped etc. cross section may be selected—then a coupling analogous to FIG. 6a and FIG. 6b is rotationally symmetrical.

Figure 6C:
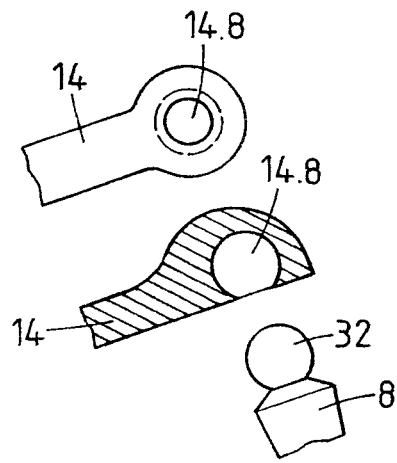
Figure 6D:
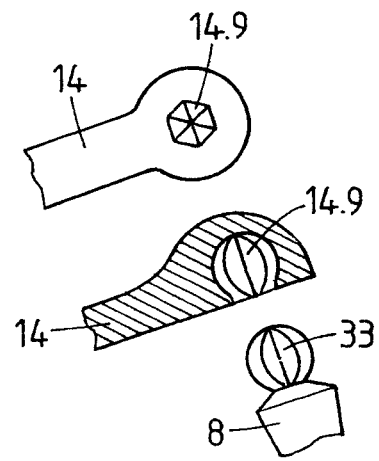

The ball socket coupling according to FIG. 6c provides the solution with regard to the proneness to angle errors. A ball element 32 of the connection piece 8 cooperates with a recess 14.8 of the oscillation element which is in the manner of a socket. This connection type is likewise not rotationally secure. However, a rotationally secure variant is also possible as shown in FIG. 6d. According to this embodiment, the connection piece 8 has a ball element which is not cylinder-symmetrical and which cooperates with a corresponding deepening 14.9 of the oscillation element. The variants according to FIGS. 6c and 6d may of course also be designed in the reverse arrangement. Further coupling variants are conceivable, for example with slightly conical pins etc.

In addition to the drawn elements, a coupling may also contain a separate arrangement, by way of which tensile forces may be transmitted onto the tool, work piece or intermediate piece. This under circumstances is necessary with embodiments, with which a fixed connection between the device and the tool, work piece or intermediate piece is desired, and with which the friction forces and/or clamping forces of the above coupling arrangement are not adequate. Such a separate arrangement, may, in the manner known per se, comprise elements engaging behind one another and running transversely to the vibration direction, for example in the manner of a bayonet locking or in another manner known per se.

Figure 7A:
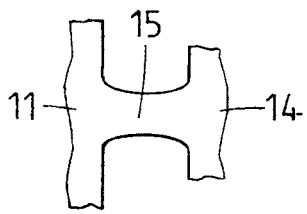
Figure 7B:
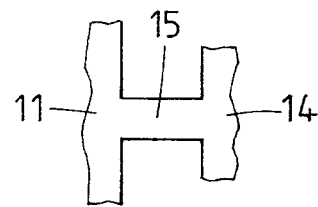
Figure 7C:
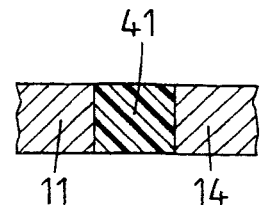
Figure 7D:
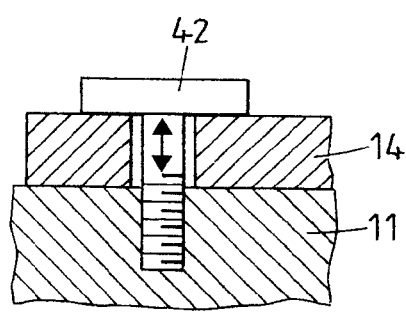
Figure 7E:
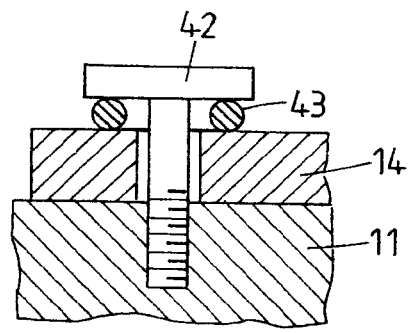

Different embodiments of connections between a fastening element 11 (or, as an alternative for embodiments which are not of one piece, the oscillation exciter) and the oscillation element 14 are drawn very schematically in the FIGS. 7a to 7e. The joint 15 according to FIG. 7a corresponds to that which has already been previously explained. FIG. 7b shows a variant thereof. According to FIG. 7c, the joint is formed by a inhomogeneity of the material at the transition between the fastening element 11 and the oscillation element 14. In the transition region 41, the sonotrode consists of a material with a modulus of elasticity which is smaller compared to the oscillation element and fastening element. According to FIG. 7d, the connection is a screw connection (as in FIG. 4), wherein the screw 42 is extendable since it has a comparatively small diameter and/or is manufactured of a material with a smaller modulus of elasticity. Instead of being a screw connection, the connection may also be effected in different comparable manners, for example as a bayonet connection. FIG. 7e finally shows a variant of a screw connection with a screw which may not be extended or not significantly extended, and a compressible spring element 43, which, for example, may be fastened on the screw. Here too, another connection arrangement is conceivable instead of a screw.

Variants with other geometries, fastening arrangements etc. are of course possible.

In this text, the part of the device which as a whole has an elongate shape, is bent and executes the actual oscillation—analogously to the two prongs of a tuning fork—have been indicated above several times as an "oscillation element". The coupling-out point is that location at which the oscillation is tapped from the oscillation element. In all illustrated embodiments, the oscillation output location coincides with the coupling-out point. This is not a necessary precondition. Differing from this, the sonotrode may, for example, comprise a transition element between the coupling-out point and the oscillation output location, and this element has any geometric shape and through which the oscillations, for example as longitudinal oscillations, may be transmitted from the coupling-out point to the oscillation output location. The coupling arrangement is then generally present at the end of the transmission element which is remote from the oscillation element. Such a transmission element may for example have the shape of a small rod which is fixedly connected to the oscillation element and permits an application of the apparatus at sunk locations.

In all previously discussed examples, the coupling-in point and the coupling-out point are located in each case in the vicinity of the ends of the oscillation element. This is not a necessity. Rather, the amplitude of the coupled-out oscillation may be influenced for example by way of the selection of the coupling-out. This is sketched by way of example in FIG. 5i by the double arrows. With a displacement of the coupling-out point from the outer end 14.2 to the inside to alternative coupling-out points 14.2', 14.2", one may reduce the amplitude in a basically infinite manner. The further the coupling-out point is applied away from the end of the oscillation element which is at the right in the figure, the smaller is the amplitude of the coupled-out oscillation. Analogously of course, the coupling-out point may be displaced along the first arm. Moreover, a counter-weight may be present distally of the coupling-out point, with which the amplitude and the resonant frequency may be influenced. (If in FIG. 5i, the coupling-out point is applied at the location 14.2", then the extra mass acts as such a counter-weight). Alternatively or in a supplementary manner, such a counter-weight may also be provided distally of the coupling-in point.

These considerations concerning the coupling-in point and coupling-out point as well as counter-weights have been discussed by way of example and by way of the embodiment example according to FIG. 5i. They analogously apply to all other oscillation element geometries.

Figure 8:
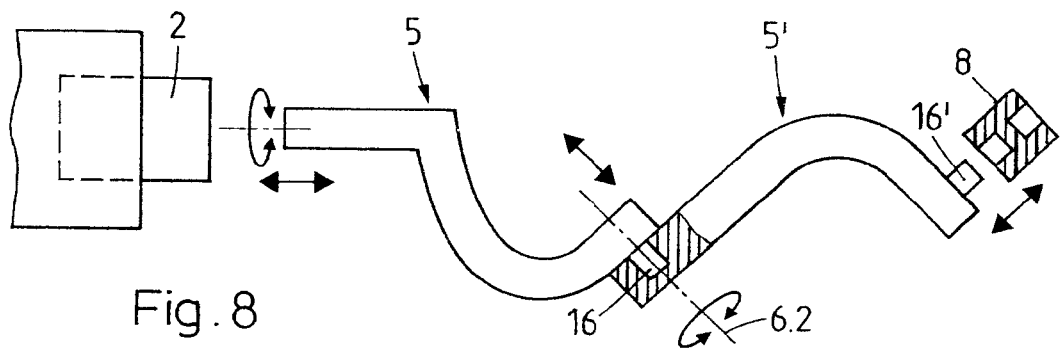

One arrangement with two devices (sonotrodes) of the type according to the invention, is drawn schematically in FIG. 8, which together form an appliance for deflecting mechanical oscillations. The first sonotrode 5 is not in direct contact with the work piece or connection piece 8, but serves as a transition piece (converter), which deflects the oscillations taken at the oscillation exciter 2, about a first deflection angle and couples them into the second sonotrode 5'. This is likewise designed according to the invention and thus deflects the oscillations about a second deflection angle. The second deflection angle with regard to the magnitude may be equally large as the first deflection angle, or the two deflection angles may be different.

The connection between the first and the second sonotrode may be fixed according to a first alternative. The orientation of the second sonotrode relative to the first may however also be influenced. For example, the orientation may be set before the operation—ex situ—and may for example be fixed with a fixation screw.

According to a further alternative, the connection is movable and the relative orientation of the sonotrode may be changeable in situ. Thus, the second sonotrode may be rotatable about the second axis 6.2 of the first sonotrode. This may, for example, be effected by way of a rotation arrangement which may be operated from the ultrasound apparatus. Such a rotation arrangement may comprise a force deflection arrangement and/or torque deflection arrangement (pull cables) in the manner known per se, which, for example, may be set in operation by an electrical drive or possibly by hand. Alternatively to this, a drive means of the rotation arrangement may also engage directly at the location of coupling between the first and the second sonotrode. For example, an oscillation which effects a rotation of the second sonotrode, similarly to the principle of a piezoelectric motor, may be activated in the first sonotrode by way of mechanical oscillations in a frequency range which is different to the operating frequency, depending on the design of the sonotrode.

Figure 9:
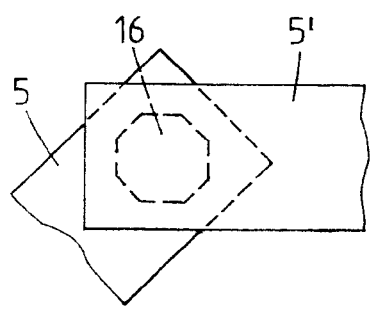

An alternative form of a coupling is drawn in FIG. 9, in which a coupling pin 16 of the one sonotrode and the corresponding recess of the other sonotrode are not cylinder-symmetrical, but for example, are rectangular in cross section. Such a coupling permits the arrangement of the two sonotrodes relative to one another in a discreet number of defined orientations. The two sonotrodes are fixed in an orientation which is selected once, and an adaptation of the orientation is only possible ex situ by way of removing the coupling pin 16 of the one sonotrode from the corresponding recess of the other sonotrode, and reintroduction in another orientation.

Figure 10:
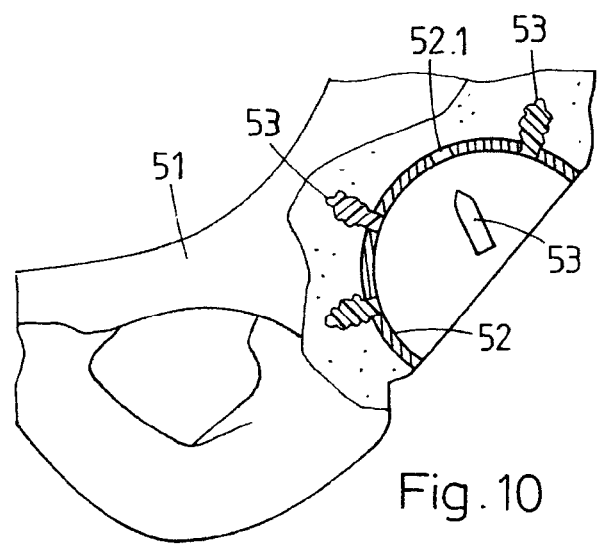

FIG. 10 shows a method, with which the sonotrode according to the invention and also the device for deflecting mechanical oscillations may be applied. A pelvis 51 is shown very schematically and sectioned, in which an artificial acetabulum 52 is applied. This is effected with a plurality of implants 53, which are designed according to the principle described in the documents WO 02/069,817 and WO 2004/017857.

In a first step, the acetabulum is placed according to methods known per se. Subsequently, implants of the mentioned type are led through the openings 52.1 envisaged for these, and are subsequently anchored in the porous bone material by way of liquefying thermoplastic or thixotropic material on their surface by way of the application of mechanical oscillations. Optionally, bores may be incorporated into the bone before the application of the mechanical oscillations, so that the introduction of the implants may be effected with little force effort. The implants may be formed such that on being subjected to mechanical oscillations, a type of head forms on the proximal side, by way of which the artificial acetabulum is fixed. Alternatively to this, a premanufactured head may also be present, and/or an infiltration of thermoplastic material of the implant into a porous surface section of the acetabulum may occur. As a further alternative, the acetabulum may comprise regions of plastic, and a welding of these regions to regions of the implant occurs.

The advantages of the invention are particularly manifest with the method according to FIG. 10, wherein the different implants must be driven into the bone at different angles. This is possible in a very simple manner by way of the deflection of mechanical oscillations with a sonotrode according to the invention. The use of a device according to FIG. 9 is particularly advantageous, in particular if the second sonotrode may be rotated relative to the first by the user with a rotation means device in situ—thus without having the remove the apparatus from the operation location.

Even if the example of an acetabulum is drawn in FIG. 10, an analogous method is also conceivable for other comparable operations, for example for a shoulder joint.

Figure 11:
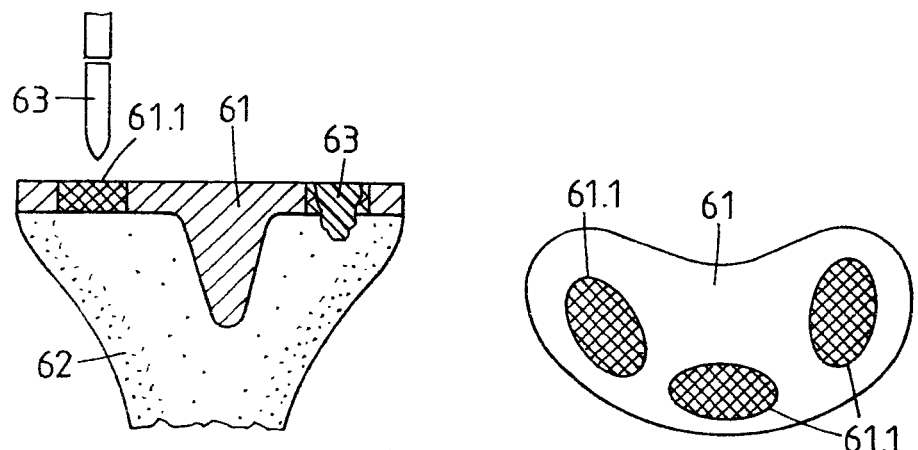

FIG. 11 shows the fixation of a tibia-plateau implant 61 according to a first variant. The tibia plateau implant 61 comprises predefined, open-pored, porous zones 61.1. In a first step it is brought into its final position on the tibia bone 62 by way of methods known per se. Subsequently, a (thermoplastic or possibly thixotropic) polymer is introduced through the porous zones 61.1 which is effected by way of subjecting a preparation 63 designed as a polymer body, to mechanical oscillations and simultaneously pressing against the porous zones. The polymer, apart from the porous zones, also infiltrates the bone and thus ensures a primary stability. The porous zones as a result are advantageous with osseo-integration and permit the tibia-plateau implant to grow well together with the bone.

A procedure which is analogous to FIG. 11—the introduction of a polymer preparation through porous zones—may also be applied if a ball socket may be fastened on the bone.

Figure 12:
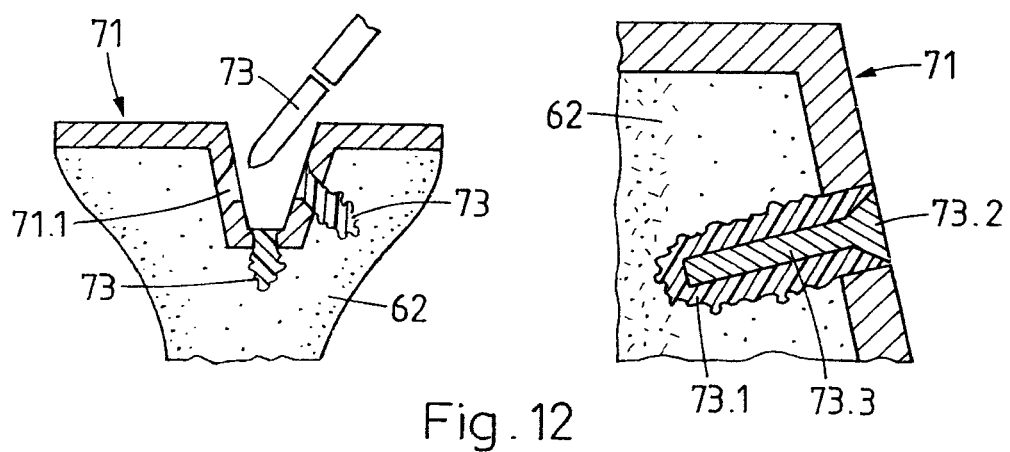

The second variant for the fixation of a tibia-plateau implant 71 on the tibia bone 62, as is shown in FIG. 12, is based on the method according to the documents WO 02/069, 817 and WO 2004/017 857. A tibia bone 62 with the tibia plateau implant 71 is drawn on the left in the figure before the implantation of a second implant 73, and on the right one can see a cut-out with an implanted implant. The tibia-plateau implant is firstly brought into its final position by way of methods known per se, which also include the operative preparation of the tibia bone. Subsequently, implants 73, whose surfaces at least partly comprise a thermoplastic or thixotropic polymer 73.1, are driven into the bone through premanufactured openings 71.1 of the tibia-plateau implant. Here too, prior bores may be optionally previously incorporated in the bone. As with the method according to FIG. 10, the implants 73 may be designed such that a type of head forms on the proximal side on being subjected to mechanical oscillation, by way of which head the artificial tibia head is fixed. Alternatively to this, a premanufactured head 73.2 may also be present, and/or an infiltration of thermoplastic material of the implant into a porous surface section of the artificial tibia head may occur, or the implant in regions may be welded to the latter. In the drawn embodiment, the implant has a hard core 73.3, for example of titanium or another suitable, non-deformable material.

The tibia head during an operation, as with those according to FIGS. 11 and 12, is accessible from the side, but mechanical oscillations and the pressure must however be applied from above or obliquely from above. For this reason, the use of a sonotrode according to the invention which deflects mechanical oscillations about a deflection angle is particularly advantageous here. A device according to FIG. 9 may also be applied.

Figure 13:
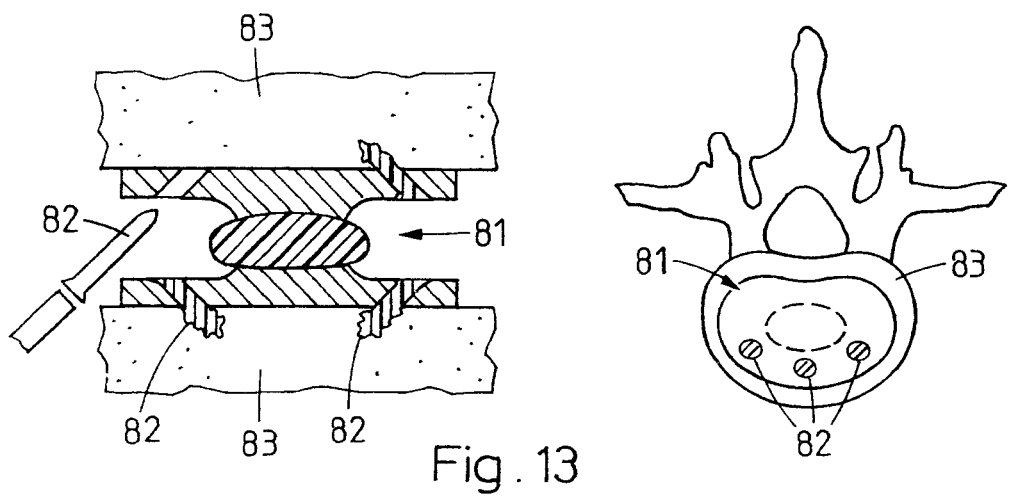
Figure 14:
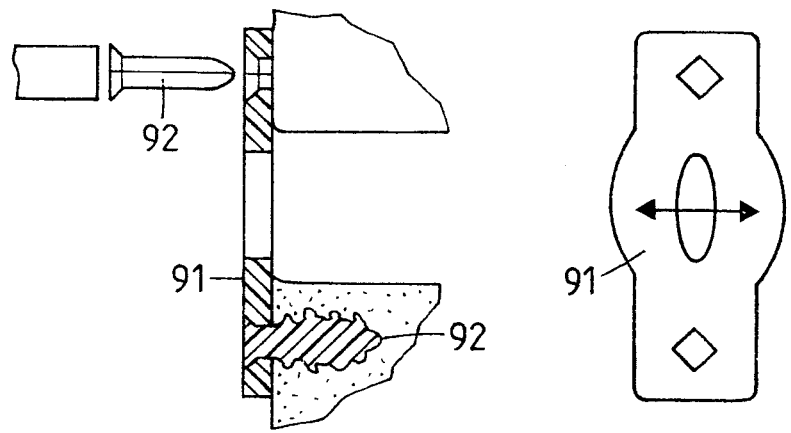

Methods from vertebral column surgery are yet shown in the FIGS. 13 and 14, which may be realised with the procedure according to the invention.

FIG. 13 shows the fixation of an artificial intervertebral disk (i.e. an intervertebral disk implant) on the vertebral bodies of the two adjacent vertebrae. A standard intervertebral disk implant may be used as an intervertebral implant 81. This is firstly placed with methods known per se between the vertebral bodies. Subsequently, implants 82 are introduced with the method according to the documents WO 02/069,817 and WO 2004/017 857, in order to fasten the implant. Thereby, polymer material which is liquefied by way of subjecting it to mechanical oscillations, infiltrates porous material of the vertebral bone 83 and according to a first variant also porous material of the intervertebral disk implant 81. According to a second variant, the polymer material of the implant 82 melts in a superficial manner with intervertebral disk implant material in the manner of an ultrasound welding. According to further variants, the fixation of the intervertebral disk implant is effected as mentioned with the previously described embodiment examples by way of a (sunk) head which is preformed, or forms on introduction.

Also with the method according to FIG. 13, the deflection of mechanical oscillations by way of the device according to the invention and, as the case may be the appliance according to the invention has a great advantage, since the implants 82 may be driven into the bone at a very difficulty accessible location and at an angle.

FIG. 14 finally shows a plate 91 which is fastened on two vertebrae and may be used for stabilising the vertebral column. The plate at least in regions is manufactured of elastic material and may be pressed together and stretched as is symbolized by the double arrow, wherein the middle part deforms. It is preferably fastened by way of implants 92 which are not circular in cross section, by which means a complete mechanical stability results even if, as a whole, only two implants 92 are used for fastening. The method which is shown in the documents WO 02/069,817 and WO2004/017 857 and discussed by way of the previous embodiment examples, is used for the fastening of the implants in the bone material, and the plate 91 on the implants.

The surgical methods shown in the above figures may in particular be minimal invasive.

The implants shown in the above figures are all based on the principle that thermoplastic material is present at least partly on their surface and this material may be liquefied in contact with hard tissue by way of mechanical oscillation. Alternatively to this drawn procedure, the implants—or at least one thereof—may also comprise a sleeve with a plurality of openings, which may not be liquefied by the mechanical vibrations, wherein liquefiable material is present in the inside of the sleeve, which is liquefied with the implantation process by way of the mechanical vibrations, and is pressed outwards through the openings in the sleeve and interpenetrates the porous structures of the hard tissue. Such implants are also known from the state of the art, for example from WO 02/069,817.

Many further surgical methods are conceivable with which the application of the sonotrode according to the invention, the device according to the invention or the apparatus according to the invention is advantageous.

The surgical methods described in the FIGS. 10-14 may also be realised with apparatus and sonotrodes producing mechanical oscillation, other than those described and claimed here, which is less preferred.

Figure 15:
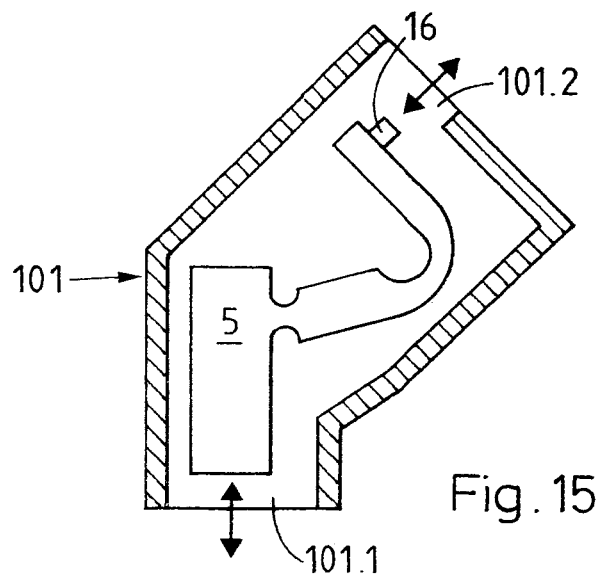

With the use of device according to the invention for surgical, dental or orthodontic methods, it may be desirable to shield tissue parts from the mechanical vibrations in order to avoid secondary damage. This may be effected by a protective housing 101, which is illustrated very schematically in FIG. 15. The protective housing may, thus, be formed such that it may be attached directly on the housing of the apparatus producing the vibrations by way of first guide means, here through a first opening 101.1, so that the relative position of the sonotrode 5 and the protective housing 101 is fixed by way of this, and no complicated vibration-decoupling mounting of the sonotrode in the protective housing is necessary. In the non-operative condition, the sonotrode may be held at its location relative to the housing by way of fixation means, from which it is decoupled in the operative condition, wherein the decoupling may be effected by way of attaching onto the sonotrode.

The protective housing particularly preferably comprises second guide means, with which holding means for the tool, the work piece or intermediate piece may be led. These are formed by a second opening 101.2 in a very schematically drawn embodiment example.

What is claimed is:

1. A device for deflecting mechanical oscillations, comprising:
   an oscillation receiver location designed for the connection of an oscillation exciter;
   an oscillation output location; and
   a bent, elongate oscillation element comprising a coupling-in point and a coupling out point,
   wherein oscillations along a first axis coupled into the oscillation receiver location set the oscillation element into transversal oscillation at the coupling-in point and cause a flexural vibration of the oscillation element,
   whereby the oscillation element transmits oscillations from the oscillation receiver location to the coupling out point, the oscillation element oscillating transversally at the coupling-out point,
   wherein transversal oscillations of the oscillation element at the coupling-out point cause an oscillation at the oscillation output location along a second axis,
   wherein the first axis and the second axis form an angle to one another,
   wherein oscillation output location comprises a coupling element equipped for the connection of a tool, a work piece, or an intermediate element, and
   wherein the device further comprises a counter element lying opposite the oscillation element with respect to the coupling-in point and influencing a resonance characteristics of the device.

2. The device according to claim 1, wherein the oscillation element and the counter mass are of one piece.

3. The device according to claim 1, further comprising an oscillation exciter portion that comprises the oscillation receiver location.

4. The device according to claim 3, wherein the oscillation exciter portion, the oscillation element and the counter-mass are all of one piece.

5. The device according to claim 1, wherein an angle between a longitudinal direction of the oscillation element at the coupling-in point and a longitudinal direction of the oscillation element at the coupling-out point is more than 90°.

6. The device according to claim 1, comprising an oscillation exciter portion, the oscillation exciter portion being connected to the coupling-in point by a joint and being one-piece with the oscillation element, wherein the oscillations that are coupled into the oscillation receiver location are longitudinal vibrations of the oscillation exciter portion.

7. The device according to claim 1, wherein the angle between the first axis and the second axis is between about 100° and about 130°.

8. The device according to claim 1, wherein the oscillation element has an essentially constant cross section over its length.

9. A device for deflecting mechanical oscillations, comprising:
   an oscillation receiver location;
   an oscillation output location; and
   an elongate oscillation element comprising a coupling-in point and a coupling out point,
   wherein oscillations along a first axis coupled into the oscillation receiver location set the oscillation element into transversal oscillation at the coupling-in point and cause a flexural vibration of the oscillation element,
   whereby the oscillation element transmits oscillations from the oscillation receiver location to the coupling out point, the oscillation element oscillating transversally at the coupling-out point,
   wherein transversal oscillations of the oscillation element at the coupling-out point cause an oscillation at the oscillation output location along a second axis,
   wherein the first axis and the second axis form an angle to one another,
   wherein oscillation output location comprises a coupling element equipped for coupling the oscillation at the oscillation output location into a tool, a work piece, or an intermediate element,
   wherein the oscillation element extends arc-shaped between the coupling-in point and the coupling-out point.

10. A device for deflecting mechanical oscillations, comprising
    an oscillation receiver location;
    an oscillation output location; and
    a bent, elongate oscillation element comprising a coupling-in point and a coupling out point,
    wherein oscillations along a first axis coupled into the oscillation receiver location set the oscillation element into transversal oscillation at the coupling-in point and cause a flexural vibration of the oscillation element,
    whereby the oscillation element transmits oscillations from the oscillation receiver location to the coupling out point, the oscillation element oscillating transversally at the coupling-out point,
    wherein transversal oscillations of the oscillation element at the coupling-out point cause an oscillation at the oscillation output location along a second axis,
    wherein the first axis and the second axis form an angle to one another,
    wherein the oscillation output location coincides with the coupling-out point and comprises a coupling element equipped for coupling the oscillation at the oscillation output location into a tool, a work piece, or an intermediate element, said coupling element extending sideways from the oscillation element with respect to an oscillation element axis.

11. The device according to claim 10, wherein the oscillation element runs in a plane and the flexural vibration of the oscillation element are oscillations in the plane.

12. The device according to claim 11, wherein the coupling element is arranged on an outer side of the bent, elongate oscillation element.

13. The device according to claim 10, wherein the coupling element is a coupling pin extending sideways away from the oscillation element and being one-piece with the oscillation element.

14. The device according to claim 10, wherein an angle between a longitudinal direction of the oscillation element at the coupling-in point and a longitudinal direction of the oscillation element at the coupling-out point is more than 90°.

15. The device according to claim 10, comprising an oscillation exciter portion, the oscillation exciter portion being connected to the coupling-in point by a joint and being one-piece with the oscillation element, wherein the oscillations that are coupled into the oscillation receiver location are longitudinal vibrations of the oscillation exciter portion.

\* \* \* \* \*